(12) United States Patent
Wall et al.

(10) Patent No.: US 10,952,738 B2
(45) Date of Patent: Mar. 23, 2021

(54) LAMINATE MEMBRANE, AN IMPLANT COMPRISING THE LAMINATE MEMBRANE AND A METHOD OF MANUFACTURING THE SAME

(71) Applicant: Clearstream Technologies Limited, Enniscorthy (IE)

(72) Inventors: Sean Wall, Enniscorthy (IE); Conor Brady, New Ross (IE); Colin Forde, Kinvara (IE); Michael Whelan, Enniscorthy (IE)

(73) Assignee: Clearstream Technologies Limited, Enniscorthy (IE)

( * ) Notice: Subject to any disclaimer, the term of this patent is extended or adjusted under 35 U.S.C. 154(b) by 0 days.

(21) Appl. No.: 16/613,737

(22) PCT Filed: May 18, 2018

(86) PCT No.: PCT/EP2018/063148
§ 371 (c)(1),
(2) Date: Nov. 14, 2019

(87) PCT Pub. No.: WO2018/211091
PCT Pub. Date: Nov. 22, 2018

(65) Prior Publication Data
US 2020/0078022 A1 Mar. 12, 2020

(30) Foreign Application Priority Data
May 18, 2017 (GB) .................................. 1708025.0

(51) Int. Cl.
*A61B 17/12* (2006.01)
*B32B 27/32* (2006.01)
(Continued)

(52) U.S. Cl.
CPC .... *A61B 17/12109* (2013.01); *A61B 17/1215* (2013.01); *B32B 27/322* (2013.01);
(Continued)

(58) Field of Classification Search
CPC .... A61B 2017/00942; A61B 17/12109; A61B 17/1215; A61B 2017/00849;
(Continued)

(56) References Cited

U.S. PATENT DOCUMENTS 5,333,620 A * 8/1994 Moutafis ............... A61M 25/09
                                                            600/585
5,585,407 A   12/1996 Patel et al.
(Continued)

FOREIGN PATENT DOCUMENTS

| EP | 2340785 A1 | 7/2011 |
| EP | 2987464 A1 | 2/2016 |

(Continued)

OTHER PUBLICATIONS

Examination Report No. 1 dated Nov. 14, 2019 pertaining to Australian Patent Application No. 2018269863.
(Continued)

*Primary Examiner* — Sarah A Simpson
(74) *Attorney, Agent, or Firm* — Dinsmore & Shohl

(57) ABSTRACT

There is provided a laminate membrane for an implant, comprising: an inner layer having an inner layer thickness; a first covering layer disposed on one side of the inner layer, the first covering layer having a first covering layer thickness; and a second covering layer disposed on another side of the inner layer, the second covering layer having a second covering layer thickness.

21 Claims, 7 Drawing Sheets

(51) Int. Cl.
    *B32B 27/40*     (2006.01)
    *A61B 17/00*     (2006.01)

(52) U.S. Cl.
    CPC .... *B32B 27/40* (2013.01); *A61B 2017/00849* (2013.01); *A61B 2017/00853* (2013.01); *A61B 2017/00862* (2013.01); *B32B 2307/728* (2013.01); *B32B 2327/18* (2013.01); *B32B 2375/00* (2013.01); *B32B 2535/00* (2013.01)

(58) Field of Classification Search
    CPC ........... A61B 2017/00853; A61B 2017/00862; B32B 27/322; B32B 27/40; B32B 2307/728; B32B 2327/18
    See application file for complete search history.

(56) References Cited

U.S. PATENT DOCUMENTS

| | | | |
|---|---|---|---|
| 5,630,844 | A | 5/1997 | Dogan et al. |
| 2004/0143292 | A1* | 7/2004 | Marino ............. A61B 17/0057 606/213 |
| 2008/0097374 | A1 | 4/2008 | Korleski et al. |
| 2011/0008529 | A1 | 1/2011 | Hossainy et al. |
| 2011/0152916 | A1* | 6/2011 | Tripp ...................... A61F 2/013 606/200 |
| 2011/0230810 | A1 | 9/2011 | Raman et al. |
| 2013/0184658 | A1* | 7/2013 | Duncan ............ A61B 17/12036 604/264 |
| 2014/0058498 | A1 | 2/2014 | Hannes et al. |
| 2014/0277346 | A1 | 9/2014 | Kanjickal et al. |
| 2015/0035957 | A1 | 2/2015 | Sheu |
| 2015/0359547 | A1* | 12/2015 | Vale ........................ A61B 17/22 606/115 |
| 2016/0166257 | A1* | 6/2016 | Allen ................. A61B 17/1215 606/200 |

FOREIGN PATENT DOCUMENTS

| | | |
|---|---|---|
| WO | 0249536 A2 | 6/2002 |
| WO | 2014140325 A1 | 9/2014 |
| WO | 2016041961 A2 | 3/2016 |

OTHER PUBLICATIONS

International Preliminary Report on Patentability dated Jun. 5, 2019 pertaining to International Application No. PCT/EP2018/063148.
Examination Report dated Sep. 15, 2020 pertaining to Australian Patent Application No. 2020202567.

* cited by examiner

US 10,952,738 B2

LAMINATE MEMBRANE, AN IMPLANT COMPRISING THE LAMINATE MEMBRANE AND A METHOD OF MANUFACTURING THE SAME

TECHNICAL FIELD

The present disclosure relates to a laminate membrane, an implant comprising the laminate membrane and a method of manufacturing the same. More specifically, the present disclosure relates to a laminate membrane having an inner layer, a first covering layer disposed on one side of the inner layer and a second covering layer disposed on another side of the inner layer.

BACKGROUND

Embolisation devices for occluding a bodily lumen are disclosed in WO 2014/140325 A1 and WO 2016/041961 A2, which are both hereby incorporated herein by reference.

Such embolisation devices may have a core and a plurality of flexible bristles which extend radially outwardly from the core. The embolisation device may also be provided with a membrane having a contracted delivery configuration and an expanded deployed configuration. The contracted delivery configuration is such that the embolisation device may be loaded into a delivery catheter allowing the embolisation device to be translated through the delivery catheter for delivery to a bodily lumen.

However, during translation through a delivery catheter, the membrane of the embolisation device may deform, for example, by folding from the initial contracted delivery configuration due to forces acting on the membrane during translation. Such forces may be exerted by the bristles of the embolisation device and/or the inner wall of the delivery catheter. Furthermore, due to this deformation of the membrane during translation through the delivery catheter, expansion of the membrane from the contracted delivery configuration to the expanded deployed configuration upon delivery to a bodily lumen may not occur in a reliable manner. In such cases, the membrane may not expand completely to its intended expanded deployed configuration or may exhibit undulations in its surface. In addition to this, the bristles neighbouring the membrane may also not expand in a reliable manner upon delivery. For example, the bristles may clump together such that they are not evenly distributed around the circumference of the device. These issues result in less occlusion of the bodily lumen, and, due to the uneven distribution of the bristles, also result in lower anchoring forces.

Accordingly, there is a need for an improved embolisation device in which deformation of the membrane during translation through the delivery catheter is minimised whilst also allowing reliable expansion of the membrane and adjacent bristles to their expanded deployed configurations.

SUMMARY

In a first aspect, there is provided a laminate membrane for an implant, comprising: an inner layer having an inner layer thickness; a first covering layer disposed on one side of the inner layer, the first covering layer having a first covering layer thickness; and a second covering layer disposed on another side of the inner layer, the second covering layer having a second covering layer thickness.

In a second aspect, there is provided an implant, comprising: the laminate membrane of the first aspect, wherein the laminate membrane is configured to have a contracted delivery configuration and an expanded deployed configuration.

In a third aspect, there is provided a method of manufacturing a laminate membrane for an implant, comprising: providing an inner layer having an inner layer thickness; providing a first covering layer on one side of the inner layer, the first covering layer having a first covering layer thickness; and providing a second covering layer on another side of the inner layer, the second covering layer having a second covering layer thickness.

BRIEF DESCRIPTION OF THE DRAWINGS

For a better understanding of the present disclosure, and to show how the same may be carried into effect, reference is made, by way of example only, to the following exemplary drawings, in which.

DETAILED DESCRIPTION

Figure 1:
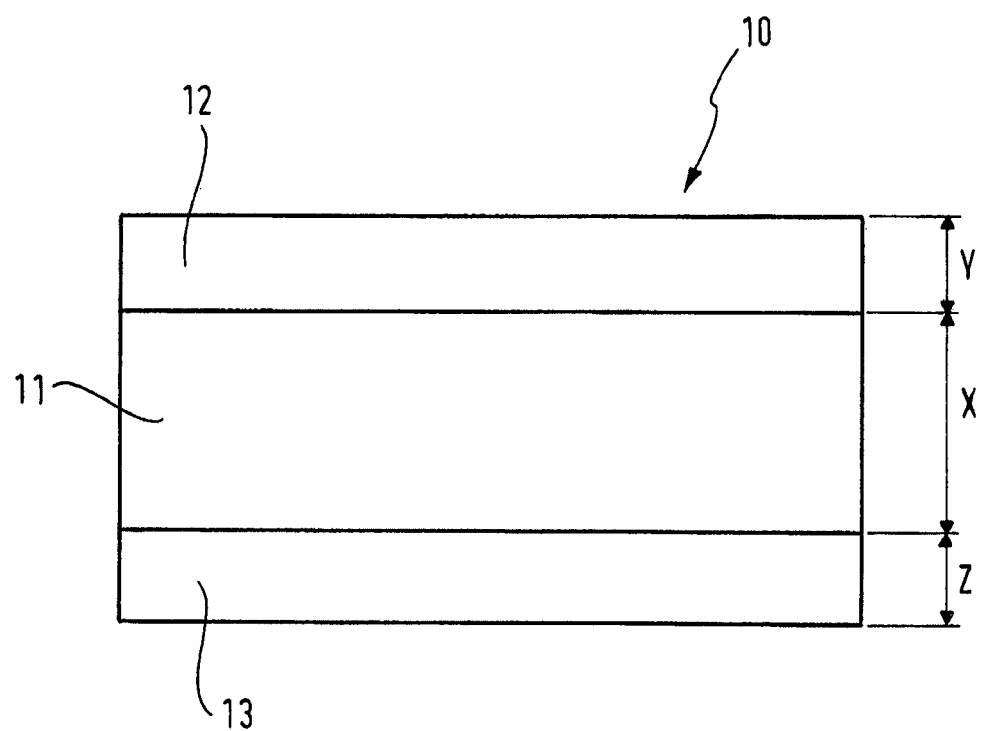
FIG. 1 shows a cross-section of a laminate membrane according to one embodiment of the present disclosure.

FIG. 1 shows a cross-section of a laminate membrane 10 according to an embodiment of the present disclosure. The laminate membrane 10 comprises an inner layer 11 having an inner layer thickness X, a first covering layer 12 having a first covering layer thickness Y and a second covering layer having a second covering layer thickness Z. The first covering layer 12 is disposed on one side of the inner layer 11. The second covering layer 13 is disposed on another side of the inner layer 11. In this embodiment, the first covering layer 12 is disposed on one side of the inner layer 11, and the second covering layer 13 is disposed on the opposite side of the inner layer 11.

Figure 6:
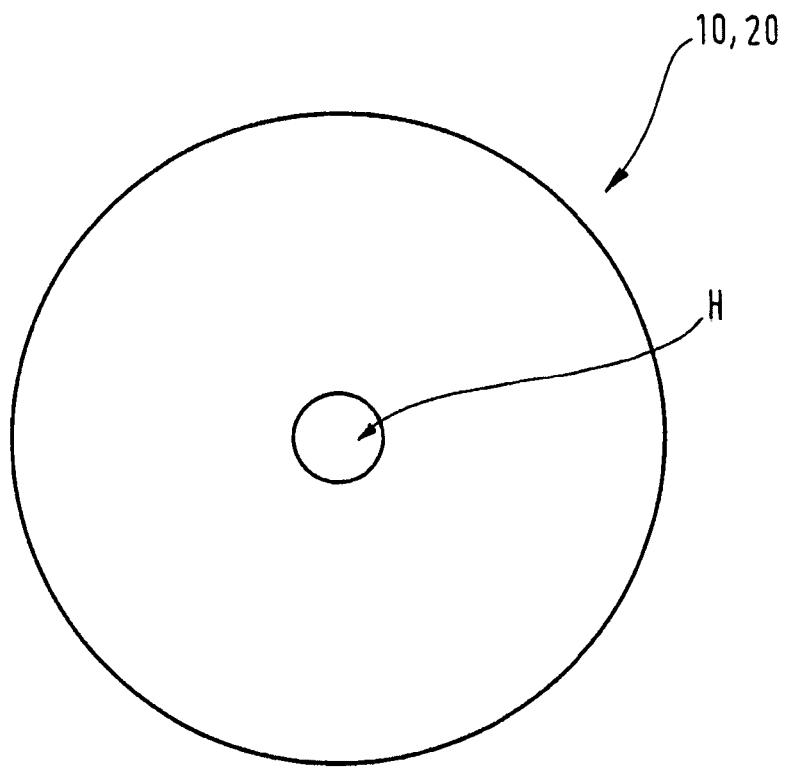
FIG. 6 shows a plan view of a laminate membrane according to embodiments of the present disclosure.

As shown in FIG. 6, laminate membrane 10 and each of the inner layer 11, first covering layer 12 and second covering layer 13 may be disc-shaped. The laminate membrane 10 may have a central through-hole H.

First covering layer 12 may entirely cover one side of the inner layer 11. Second covering layer 13 may entirely cover the other side of the inner layer 12.

The laminate membrane 10 may be configured to have a contracted delivery configuration and an expanded deployed configuration. In the contracted delivery configuration (see FIG. 5), the laminate membrane 10 forms a conical shape with a smaller radial extent than in the expanded deployed configuration (see FIG. 4).

The inner layer 11 provides the backbone of the laminate membrane 10 which provides structural properties of the laminate membrane 10 such as stiffness and elasticity. In this embodiment, the first covering layer 12 and the second covering layer 13 are outermost surface layers of the laminate membrane 10. The first covering layer 12 and the second covering layer 13 dictate the properties of the outer surface of the laminate membrane 10 such as the frictional properties and surface energy.

The first covering layer 12 and the second covering layer 13 may each be made from a lower friction material than the material from which the inner layer 11 is made.

The skilled person will be aware of many different ways of determining whether a material is a lower friction material than another material. For example, the materials to be compared may be formed so as to have flat surfaces, and the surface energy, surface roughness, or static coefficient of friction (relative to itself or another common surface) of these surfaces may be measured, as would be understood by the skilled person. The flat surfaces of each of the materials being tested may be formed by the same process (e.g. each formed by electrospinning, extrusion, film casting, dip casting, spin casting, spray deposition or vapour deposition).

In other words, at least one of the first covering layer 12 and the second covering layer 13 are made of a material which exhibit a lower surface roughness or static coefficient of friction (measured relative to itself or another common surface) than the material from which the inner layer 11 is made of.

The stiffness of the inner layer 11 may be greater than the stiffness of each of the first covering layer 12 and the second covering layer 13.

The elasticity of the first covering layer 12 and/or the second covering layer 13 may be higher than or equal to the elasticity of the inner layer 11. In such cases, the laminate membrane 10 may allow for a contracted delivery configuration with a lower radial profile without risk of permanent deformation as the first covering layer 12 and/or the second covering layer 13, which experience greater elongation during bending of the laminate membrane 10 than the inner layer 11, are better able to stretch relative to the inner layer 11.

Various materials may be used for the inner layer 11, first covering layer 12 and the second covering layer 13.

For example, the inner layer 11 may consist of polyurethane (PU) and each of the first covering layer 12 and the second covering layer 13 may consist of polytetrafluoroethylene (PTFE). In this case, the inner layer 11 of PU provides high stiffness to the laminate membrane 10, whereas the first covering layer 12 and the second covering layer 13 of PTFE result in the outer surface of the laminate membrane 10 having low friction. The high stiffness may allow the laminate membrane 10 to reliably transition from the contracted delivery configuration to the expanded deployed configuration, whilst the low friction surfaces may reduce deformation during translation.

In this embodiment, first covering layer thickness Y and second covering layer thickness Z are the same, and the first covering layer thickness Y and the second covering layer thickness Z are each smaller than the inner layer thickness X.

The inner layer thickness X may be between 4 to 8 μm, and the first covering layer thickness Y and the second covering layer thickness Z may be between 1 to 3 μm. In another embodiment, the inner layer thickness X may be between 6 to 10 μm, and the first covering layer thickness Y and the second covering layer thickness Z may be between 1 to 4 μm.

The laminate membrane 10 may be manufactured by providing the inner layer 11, providing the first covering layer 12 on one side of the inner layer 11, and providing a second covering layer 13 on another side of the inner layer 11. Each of the inner layer 11, first covering layer 12 and the second covering layer 13 may be deposited using electrospinning.

Figure 2:
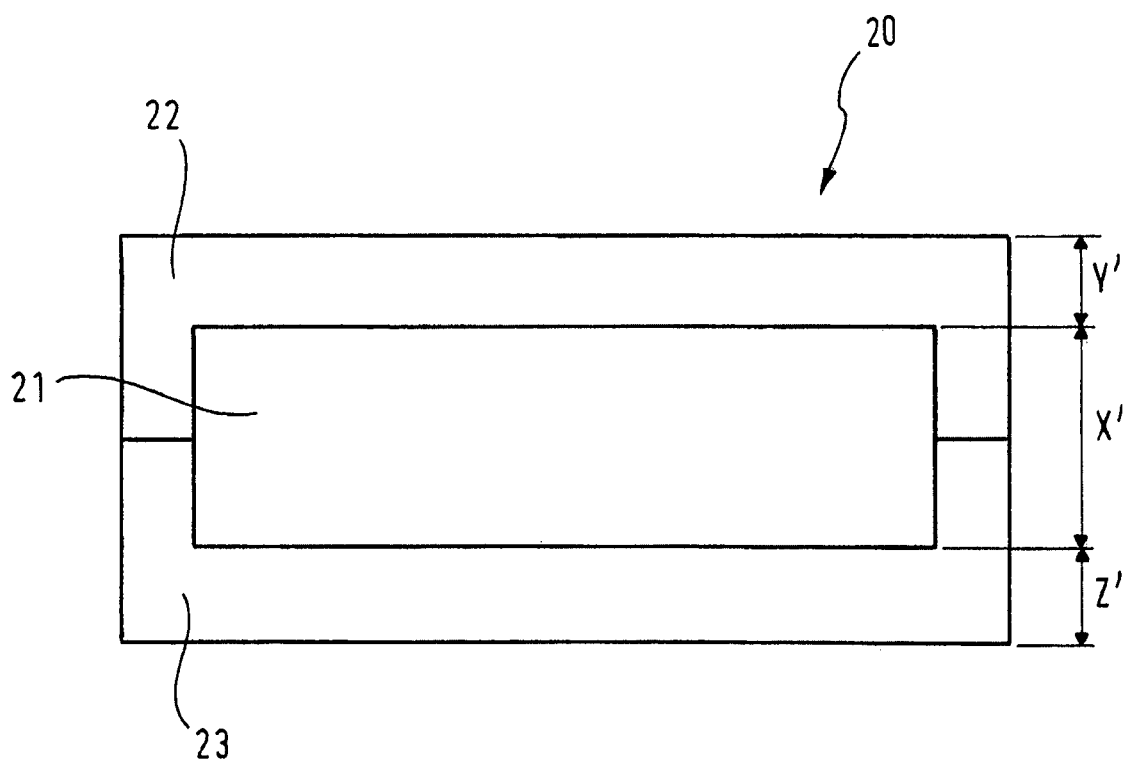
FIG. 2 shows a cross-section of a laminate membrane according to another embodiment of the present disclosure.

FIG. 2 shows a cross-section of a laminate membrane 20 according to another embodiment comprising an inner layer 21 having an inner layer thickness X', a first covering layer 22 having a first covering layer thickness Y' and a second covering layer 23 having a second covering layer thickness Z'. The first covering layer 22 is disposed on one side of the inner layer 21. The second covering layer 23 is disposed on the opposite side of the inner layer 21.

The inner layer thickness X' may be between 4 to 8 μm, and the first covering layer thickness Y' and the second covering layer thickness Z' may be between 1 to 3 μm. In another embodiment, the inner layer thickness X' may be between 6 to 10 μm, and the first covering layer thickness Y' and the second covering layer thickness Z' may be between 1 to 4 μm.

Laminate membrane 20 is similar to laminate membrane 10 shown in FIG. 1, except that first covering layer 22 and second covering layer 23 also cover the outer edge surface of the inner layer 11. In particular, first covering layer 22 and second covering layer 23 also cover the curved edge surface of the inner layer 11. Hence, the first covering layer 22 and the second covering layer 23 together cover all external surfaces of the inner layer 21.

Figure 3:
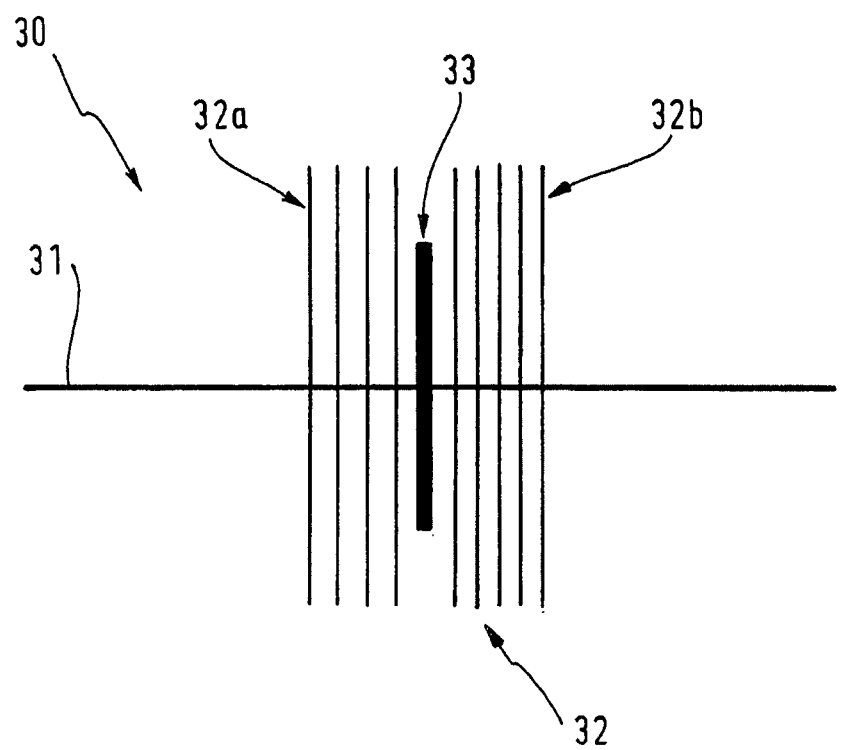
FIG. 3 shows an embolisation device with a laminate membrane according to an embodiment of the present disclosure.

FIG. 3 shows an embolisation device 30 according to an embodiment of the present disclosure. The embolisation device 30 has a longitudinally extending core 31 and a plurality of flexible bristles 32 extending outwardly from the core, the flexible bristles 32 are configured to have a contracted delivery configuration and an expanded deployed configuration in which the flexible bristles 32 extend generally radially outwardly from the core to anchor the device in a bodily lumen. The flexible bristles 32 may be configured to be resilient such that they are biased from their contracted delivery configuration to their expanded deployed configuration.

The embolisation device 30 also has a laminate membrane 33 disposed on the core 31. The laminate membrane 33 may be any of the laminate membranes described herein. The laminate membrane 31 may have a through-hole which allows the core 31 to pass through the laminate membrane 31. The laminate membrane 33 is configured to occlude flow through the bodily lumen.

The laminate membrane 30 is positioned on the core 31 within a segment of flexible bristles 32. Some flexible bristles 32a are disposed proximally adjacent to one side of the laminate membrane 33 and some flexible bristles 32b are disposed distally adjacent to the opposite side of the laminate membrane 33.

Figure 4:
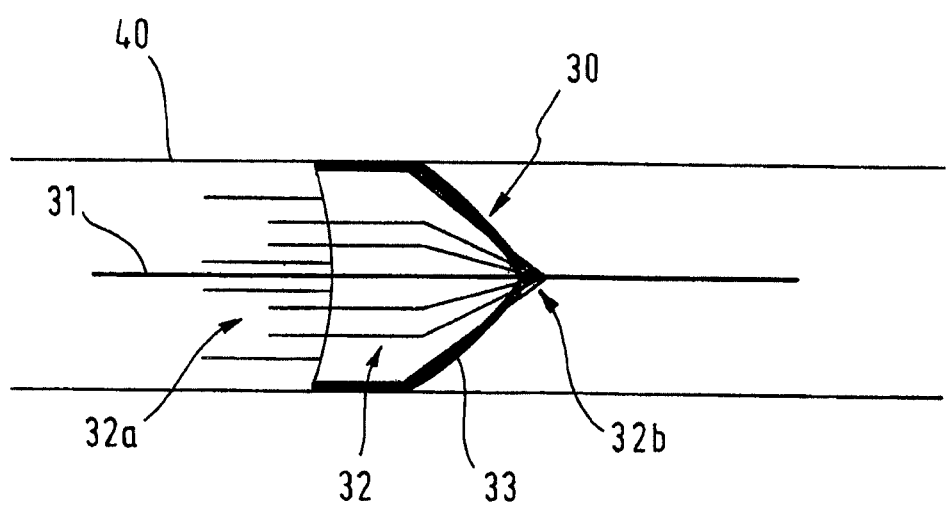
FIG. 4 shows the embolisation device shown in FIG. 3 in an expanded deployed configuration in a bodily lumen.

FIG. 4 shows the embolization device 30 in its expanded deployed configuration in a bodily lumen 40, where the flexible bristles 32 and the laminate membrane 33 are in their expanded deployed configurations. In this configuration, the laminate membrane 33 occludes flow through the bodily lumen 40. The flexible bristles 33 anchor the embolisation device 30 in the bodily lumen 40, preventing migration of the embolisation device 30.

The orientation of the expanded laminate membrane 33 in its expanded deployed configuration and the orientation of the expanded flexible bristles 32 in the expanded deployed configuration is the same. For example, both the laminate membrane 33 and the adjacent flexible bristles 32 may be deployed pointing distally or proximally.

Figure 5:
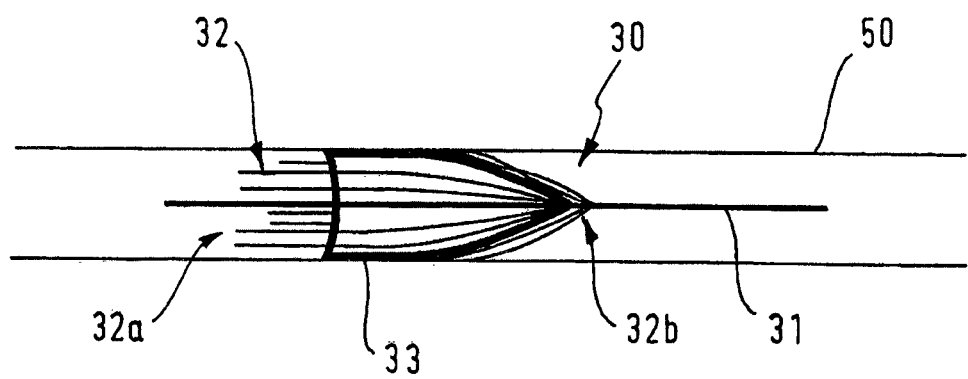
FIG. 5 shows the embolisation device shown in FIG. 3 in a contracted delivery configuration within a delivery catheter.

FIG. 5 shows the embolization device 30 in its contracted delivery configuration in a delivery catheter 50, where the flexible bristles 32 and the laminate membrane 33 are in their contracted delivery configurations. When the flexible bristles 32 and the laminate membrane 33 are in their contracted delivery configurations, at least a portion of the laminate membrane 31 contacts the delivery catheter. In the contracted delivery configuration, the embolisation device 30 may be translated through the delivery catheter 50.

The orientation of the collapsed laminate membrane 33 in its contracted delivery configuration and the orientation of the collapsed flexible bristles 32 in the contracted delivery configuration is the same. For example, both the laminate membrane 33 and the adjacent flexible bristles 32 may be collapsed pointing distally or proximally.

Using any of the laminate membranes as described herein may provide an embolisation device 30 in which deformation of the membrane 33 during translation through the delivery catheter is minimised whilst also allowing reliable expansion of the membrane 33 and adjacent bristles 32 to their expanded deployed configurations.

Although the above explanation is considered to fully clarify how the present disclosure may be straight-forwardly put into effect by those skilled in the art, it is to be regarded as purely exemplary. In particular, there are a number of variations which are possible, as may be appreciated by those skilled in the art.

For example, even though the above laminate membranes are disc-shaped, they may be of any shape such as rectangular, square or cylindrical.

Further, even though the above laminate membranes are described in relation to an embolisation device with a core and a plurality of flexible bristles, laminates according to the present disclosure are also applicable to any type of embolisation device.

Specifically, according to an aspect of the present disclosure, there is provided an embolisation device, comprising: a laminate membrane as described herein.

In an embodiment, the laminate membrane is configured to have a contracted delivery configuration and an expanded deployed configuration. The embolisation device may comprise an embolisation coil. The laminate membrane may be disposed around at least part of the embolisation coil. At least a part of the laminate membrane may be disposed between adjacent turns in the embolisation coil.

Furthermore, even though the above laminate membranes are described in relation to embolisation devices, laminate membranes according to the present disclosure are also applicable to any type of medical implant, and, in particular, a medical implant with a contracted delivery configuration and an expanded deployed configuration, where the medical implant is configured to be delivered to a bodily lumen in the contracted delivery configuration. For example, the laminate membranes according to the present disclosure are particularly suited to expandable stents. Using the laminate membranes of the present disclosure may reduce deformation of the membrane during translation through the delivery catheter whilst also allowing reliable expansion of the membrane to its expanded deployed configuration.

Further, each of the inner layer, first covering layer and the second covering layer may be made from various materials. For example, the inner layer may be made from a composite of polyurethane and one or more other materials. In particular, the inner layer may be made from a polyurethane and polytetrafluoroethylene composite or a copolymer of 90% 55D polyurethane and 10% silicone, by weight. In other embodiments, the inner layer 11 may comprise, or consist of, condensed PTFE or fluorinated ethylene propylene (FEP).

Each of the first covering layer and the second covering layer may be made from a composite of materials. The first covering layer and the second covering layer may be made from different materials from each other. First covering layer may be made from: a hydrophobic material such as polytetrafluoroethylene and/or ultra-high molecular weight polyethylene; a hydrophilic material; and/or silicone. The second covering layer may be made from: a hydrophobic material such as polytetrafluoroethylene and/or ultra-high molecular weight polyethylene; a hydrophilic material; and/or silicone.

Further, the structural properties of the inner layer, first covering layer and the second covering layer may be varied from the above. In particular, the inner layer may have higher elastic recovery, tear-resistance and/or permeability than at least one of the first covering layer and the second covering layer. At least one of the first covering layer and the second covering layer may have lower surface energy than the inner layer.

In the above embodiments, the inner layer, the first covering layer and the second covering layer are each single layers. However, in alternative embodiments, the inner layer, the first covering layer and/or the second covering layer may each be formed of multiple sub-layers.

Figure 7:
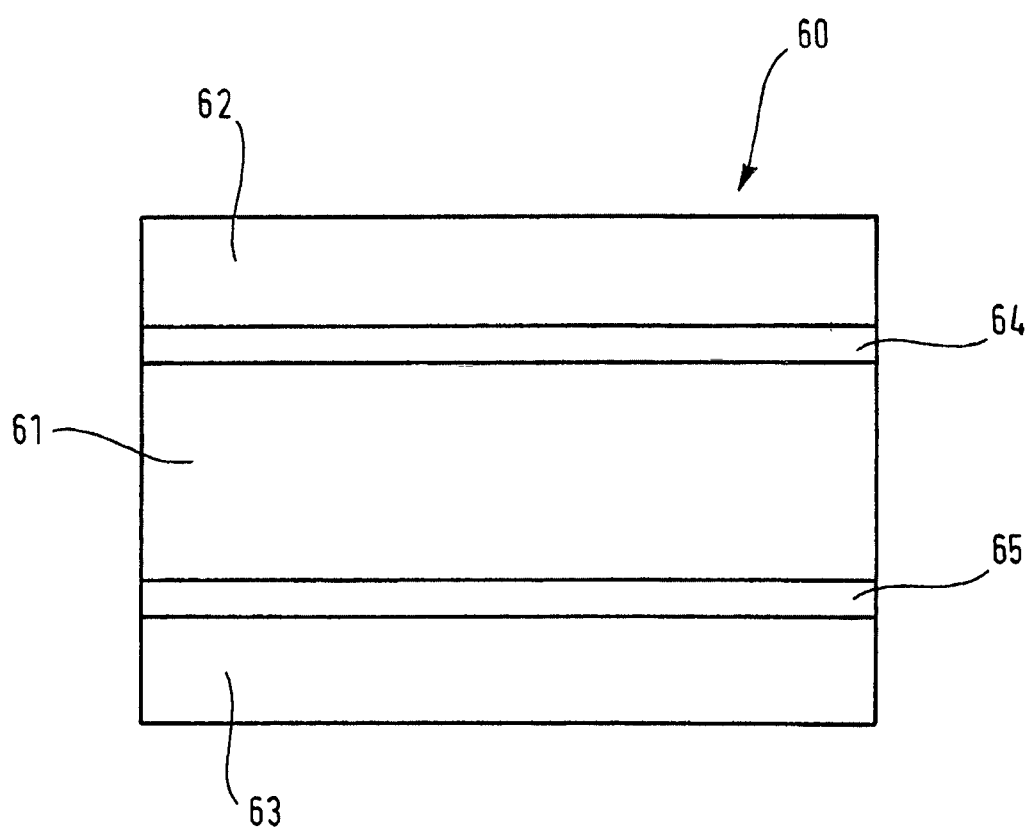
FIG. 7 shows a cross-section of a laminate membrane according to another embodiment of the present disclosure.

Further, the above laminate membranes may further comprise a tie-layer disposed between the inner layer and one or each of the first covering layer and the second covering layer. Such a tie-layer may increase the adherence between the layers. As an example, such a tie-layer may be DuPont™ Bynel®. The tie-layers may be made from: modified ethylene vinyl acetate polymer; acid modified ethylene acrylate resin; anhydride modified ethylene acrylate resin; or anhydride-modified linear low-density polyethylene resin. Generally, the tie-layers may be made from ethylenes including acetates & acrylates thereof. FIG. 7 shows an exemplary embodiment of a laminate membrane 60 comprising tie-layers 64, 65. The laminate membrane 60 is similar to laminate membrane 10 in that in has an inner layer 61, first covering layer 62 and second covering layer 63. However, laminate membrane 60 has a first tie-layer 64 disposed between the inner layer 61 and the first covering layer 62, and a second tie-layer 65 disposed between the inner layer 61 and the second covering layer 63.

In some embodiments, the inner layer and the first covering layer and/or the second covering layer may be chemically or electrostatically adhered to each other.

Furthermore, even though the above manufacturing method uses an electrospinning process for forming each of the layers, various other manufacturing methods may be used. For example, the layers may be formed by electrospinning, extrusion, film casting, dip casting, spin casting, spray deposition or vapour deposition. Furthermore, different layers may be formed by different methods. For example, the inner layer may be formed from dip casting or spray casting. The first covering layer and the second covering layer may each be formed by electrospinnning onto the inner layer.

All of the above are fully within the scope of the present disclosure, and are considered to form the basis for alternative embodiments in which one or more combinations of the above described features are applied, without limitation to the specific combinations disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptions fall within the scope of the present disclosure.

The invention claimed is:

1. A laminate membrane for an implant, comprising:
an inner layer having an inner layer thickness;
a first covering layer disposed on one side of the inner layer, the first covering layer having a first covering layer thickness; and
a second covering layer disposed on another side of the inner layer, the second covering layer having a second covering layer thickness;
wherein:
the inner layer comprises a polyurethane and polytetrafluoroethylene composite, at least one of the first covering layer and the second covering layer comprises a hydrophilic material;
a hole is formed through each of the inner layer, the first covering layer, and the second covering layer configured to receive a stem of an embolisation device and be mounted thereto; and
each of the layers are configured to be implanted within a body and have a contracted delivery configuration and an expanded deployed configuration configured to diametrically occlude flow through a bodily lumen between the stem and the bodily lumen and form an embolisation,
wherein the stiffness of the inner layer is greater than the stiffness of at least one of the first covering layer and the second covering layer.

2. The laminate membrane of claim 1, wherein at least one of the first covering layer and the second covering layer is made from a lower friction material than the material from which the inner layer is made.

3. The laminate membrane of claim 1, wherein the elasticity of at least one of the first covering layer and the second covering layer is higher than or equal to the elasticity of the inner layer.

4. The laminate membrane of claim 1, wherein at least one of the first covering layer and the second covering layer is an outer surface layer of the laminate membrane.

5. The laminate membrane of claim 1, wherein at least one of the inner layer, the first covering layer and the second covering layer is made from electrospinning, extrusion, film casting, dip casting, spin casting, spray deposition or vapour deposition.

6. The laminate membrane of claim 1, wherein the inner layer has at least one of a higher elastic recovery, tear-resistance and permeability than at least one of the first covering layer and the second covering layer.

7. The laminate membrane of claim 1, wherein at least one of the first covering layer and the second covering layer has lower surface energy than the inner layer.

8. The laminate membrane of claim 1, wherein the inner layer thickness is between 4 to 8 µm, and at least one of the first covering layer thickness and the second covering layer thickness is between 1 to 3 µm.

9. The laminate membrane of claim 1, wherein the inner layer thickness is between 6 to 10 µm, and at least one of the first covering layer thickness and the second covering layer thickness is between 1 to 4 µm.

10. The laminate membrane of claim 1, wherein a first surface of the inner layer is in contact with a surface of the first covering layer, and wherein at least one of the first surface of the inner layer and the surface of the first covering layer has a texture feature configured to mechanically adhere the inner layer and the first covering layer.

11. The laminate membrane of claim 10, wherein a second surface of the inner layer is in contact with a surface of the second covering layer, and wherein at least one of the second surface of the inner layer and the surface of the second covering layer has a texture feature configured to mechanically adhere the inner layer and the second covering layer.

12. The laminate membrane of claim 10, wherein the texture feature is formed by mechanical etching, chemical etching, plasma etching or corona etching.

13. The laminate membrane of claim 1, comprising at least one of a tie-layer between the inner layer and the first covering layer and a tie-layer between the inner layer and the second covering layer.

14. The laminate membrane of claim 1, wherein at least one of the first covering layer thickness and the second covering layer thickness is less than the inner layer thickness.

15. The laminate membrane of claim 1, wherein at least one of the first covering layer and the second covering layer entirely covers the one side or the another side of the inner layer, respectively.

16. The laminate membrane of claim 15, wherein the first covering layer and the second covering layer together cover all external surfaces of the inner layer.

17. The laminate membrane of claim 1, wherein the stiffness of the inner layer is between 0.9 to 2.5 GPa, alternatively between 1.1 to 2.3 GPa, and alternatively between 1.3 to 2.1 GPa.

18. The laminate membrane of claim 1, wherein the stiffness of at least one of the first covering layer and the second covering layer is between 0.1 to 0.75 GPa, alternatively between 0.25 to 0.65 GPa, and alternatively between 0.4 to 0.55 GPa.

19. The laminate membrane of claim 1, wherein the first covering layer is a different material from the second covering layer.

20. A method of manufacturing the laminate membrane claim 1, comprising:
providing the inner layer;
providing the first covering layer on one side of the inner layer; and
providing the second covering layer on another side of the inner layer.

21. The method of claim 20, wherein at least one of the inner layer, the first covering layer and the second covering layer is made from electrospinning, extrusion, film casting, dip casting, spin casting, spray deposition or vapour deposition.

* * * * *

UNITED STATES PATENT AND TRADEMARK OFFICE
CERTIFICATE OF CORRECTION

Page 1 of 1

PATENT NO. : 10,952,738 B2
APPLICATION NO. : 16/613737
DATED : March 23, 2021
INVENTOR(S) : Sean Wall et al.

It is certified that error appears in the above-identified patent and that said Letters Patent is hereby corrected as shown below:

On the Title Page

Item (54), and in the Specification, Column 1, Lines 1-4, title of invention, delete "LAMINATE MEMBRANE, AN IMPLANT COMPRISING THE LAMINATE MEMBRANE AND A METHOD OF MANUFACTURING THE SAME" and insert --A LAMINATE MEMBRANE, AN IMPLANT COMPRISING THE LAMINATE MEMBRANE AND A METHOD OF MANUFACTURING THE SAME--, therefor.

Item (71), applicant 1, city, delete "Enniscorthy" and insert --Enniscorthy, County Wexford--, therefor.

Item (72), inventor 3, city, delete "Kinvara" and insert --Ballycleary, Kinvara Galway--, therefor.

Item (73), assignee 1, city, delete "Enniscorthy" and insert --Enniscorthy, County Wexford--, therefor.

In page 2, Column 2, item (56), U. S. patent documents, cite no. 8, delete "Allen" and insert --Allen et al.--, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*